United States Patent [19]
Collin

[11] Patent Number: 5,985,330
[45] Date of Patent: Nov. 16, 1999

[54] INHIBITION OF ANGIOGENESIS BY SEA CUCUMBER FRACTIONS

[75] Inventor: Peter Donald Collin, Sunset, Me.

[73] Assignee: Coastside Bio Resources, Stonington, Me.

[21] Appl. No.: 08/880,359

[22] Filed: Jun. 23, 1997

Related U.S. Application Data

[63] Continuation-in-part of application No. 08/692,175, Aug. 5, 1996, abandoned.
[51] Int. Cl.$^6$ .......................... A61K 35/56; A61K 31/70; A61K 31/715; A61K 38/02
[52] U.S. Cl. .......................... 424/520; 424/572; 424/574; 514/2; 514/21; 514/24; 514/25; 514/42; 514/53; 514/54
[58] Field of Search .................................... 424/520, 572, 424/574; 514/54, 24, 25, 42, 2, 53, 21

[56] References Cited

U.S. PATENT DOCUMENTS 4,996,159  2/1991  Glaser .................................... 435/70.3

FOREIGN PATENT DOCUMENTS 295037  8/1993  European Pat. Off. .

OTHER PUBLICATIONS

Mourao et al., Trends in Glycoscience and Glycotechnology, 7:235–246, 1995.
Vieira et al., Biochemistry, 32:2254–2262, 1993.
Hahnenberger et al. Glycoconjugate Journal, 8:350–353, 1991.
Treherne, J.E. et al., Ion–Dependent Viscosity of Holothurian Body Wall and its Implications for the Functional Morphology of Echinoderms. *J. Exp. Biol.* 99:1–8 (1982).
Findlay, John A. et al., Frondogenin, A New Aglycone From the Sea Cucumber *Cucumaria frondosa*. *J. Natural Products*, 47(2):320–324, Mar.–Apr. (1984).
Tanaka, N.G. et al., Inhibitory Effects of Anti–Angiogenic Agents on Neovascularization and Growth of the Chorioallantoic Membrane (CAM). The Possibility of a New CAM Assay for Angiogenesis Inhibition. *Exp. Pathol.*, 30:143–150 (1986).
Folkman, Judah et al., Angiogenesis Inhibition and Tumor Regression Caused by Heparin or a Heparin Fragment in the Presence of Cortisone. *Science*, 221:719–725 (1983).
Robin, Jeffrey B., The Histopathology of Corneal Neovascularization. *Arch. Ophthalmol.*, 103:284–287 (1985).
Kalyani, G.A. et al., Holothurin—A Review. *Indian J. Nat. Prod.*, 4, (2), 3 (1988).
Anisimov, M.M. et al., Comparative Study of Cytotoxic Activity of Triterpene Glycosides From Marine Organisms. Toxicon, vol. 18, pp. 221–223 (1980).
Rodriguez, J. et al., Holothurinosides: New Antitumour Non Sulphated Triterpenoid Glycosides From the Sea Cucumber *Holothuria forskilii*. Tetrahedron, vol. 47, No. 26, pp. 4753–4762 (1991).
Miyamoto, T. et al., Six Newly Identified Biologically Active Triterpenoid Glycoside Sulfates from the Sea Cucumber *Cucumaria echinata*. Liebigs Ann. Chem., 1990, 453–460 (1989).
Santhakumari, G., Antimitotic Effects of Holothurin. *Cytologia* 53: 163–168 (1988).
Pettit, George R. et al., Antineoplastic Agents XLV: Sea Cucumber Cytotoxic Saponins. *Journal of Pharmaceutical Sciences*, vol. 65, No. 10: 1558–1559 (1976).

*Primary Examiner*—Michael G. Wityshyn
*Assistant Examiner*—Janet M. Kerr
*Attorney, Agent, or Firm*—Rothwell, Figg, Ernst & Kurz

[57] ABSTRACT

The present invention provides inhibition of angiogenesis in a warm-blooded animal by the administration of preparations isolated from the echinoderm sea cucumber (Class Holothuroidea). This preparation is useful as a therapeutic agent against malignant tumors and as a preventive or therapeutic drug against various diseases, such as rheumatoid arthritis, caused by vascular hyperplasia.

40 Claims, 2 Drawing Sheets

INHIBITION OF ANGIOGENESIS BY SEA CUCUMBER FRACTIONS

This is a continuation-in-part application of pending application Ser. No. 08/692,175, filed on Aug. 5, 1996, now abandoned.

FIELD OF THE INVENTION

The present invention relates to compositions for inhibiting angiogenesis in warm-blooded animals. More particularly, the present invention relates to the inhibition of angiogenesis by administering distinct fractions of the echinoderm sea cucumber which comprise:

1. the isolated body wall of the sea cucumber, or its active derivatives,
2. the epithelial layer of the sea cucumber body wall, or its active derivatives,
3. the anterior flower or mouth portion of the sea cucumber, or its active derivatives, or
4. combinations thereof.

BACKGROUND OF THE INVENTION

Progress or metastasis of malignant tumors and such diseases as rheumatoid arthritis, diabetic retinopathy, retinopathy of prematurity, senile macular degeneration, neovascular glaucoma, retrolental fibroplasia, neovascular glaucoma, psoriasis, angiofibromas, immune and non-immune inflammation, capillary proliferation within atherosclerotic plaques, hemangiomas, Kaposi's Sarcoma, endometriosis, and hypergeneration of scars after wound healing are now known to be caused by hyperplasia of the blood vessel (particularly the peripheral capillary vessel). As preventive or therapeutic medicines against these diseases and conditions, various neovascularization inhibitors containing angiogenesis-inhibiting substances as active effective ingredients have been developed. The angiogenesis-inhibiting substances reported to date include, for example, medroxyprogesterone (Ashiya, et al: Int. J. Cancer, 1989, 44, 895), sulfated protamine (Ogawa et al: Exp. Pathol., 1986, 30, 143), combination of heparin and cortisone (J. Folkman, et al: Science, 1983, 221, 719), prednisolone acetate (J. B. Robin: Arch. Opthalmol., 19855, 103, 284), herbimycin A (Japanese Patent Provisional Publication No. 295, 509/88), peptide from retinal pigment epithelial cell (U.S. Pat. No. 4,996,159), sulfated polysaccharide (U.S. Pat. No. 4,900, 815), and phenol derivatives (EP-A-295,037). These angiogenesis-inhibiting substances are not, however, completely satisfactory as preventive or therapeutic medicaments against the above-mentioned diseases and conditions because of the insufficient inhibitory effect of angiogenesis in some cases.

There has been much scientific interest in the search for new inhibitors of angiogenesis because of the hope that this inhibition of new blood vessels would limit the growth of neoplastic tumors which depend on new vascular growth. As a normal cell develops into a solid tumor it undergoes a series of changes. At the physiological level, growth is enhanced, immunity evaded, and neovascularization induced. Neovascularization or angiogenesis appears to be a prerequisite. Experimental solid tumors are unable to grow beyond a few millimeters in thickness without a blood supply. Most natural solid tumors elaborate angiogenic factors that attract the new vessels on which they depend. It has become increasingly evident that once a solid tumor has been established in the body, every increase in tumor cell population must be preceded by an increase in new capillaries that converge upon the tumor. Consequently, there has been a continuing research effort directed toward the question of what prevents rampant capillary proliferation and what maintains the quiescent state of the capillary endothelial cells of normal tissues. There has also been an active search for a therapeutic agent or agents which can cause capillary regression. Identification of such an agent has proven to be a very difficult problem. About the only demonstrable difference between tumor angiogenesis and other types of non-neoplastic angiogenesis is a greater intensity and persistence of the angiogenesis induced by tumors.

There is a generally recognized lack of a therapeutic agent which can effectively inhibit tumor neovascularization and limit or even completely stop the growth of tumors.

SUMMARY OF THE INVENTION

This invention provides a method of inhibiting angiogenesis in a warm-blooded animal in need of such treatment which comprises administering to said warm-blooded animal a therapeutically effective amount of a composition comprising the isolated body wall of a sea cucumber, the isolated epithelial layer of the body-wall of the sea cucumber, the flower of the sea cucumber, their active derivatives or mixtures thereof.

It has been found that these portions of the sea cucumber dramatically inhibit angiogenesis, vascularization and tubule formation, in in vivo assays which are known in the medical field as being acceptable in providing relevant data and valid indications of therapeutic efficacy for subsequent development and medical use of active compositions.

DETAILED DESCRIPTION OF THE INVENTION

Figure 1:
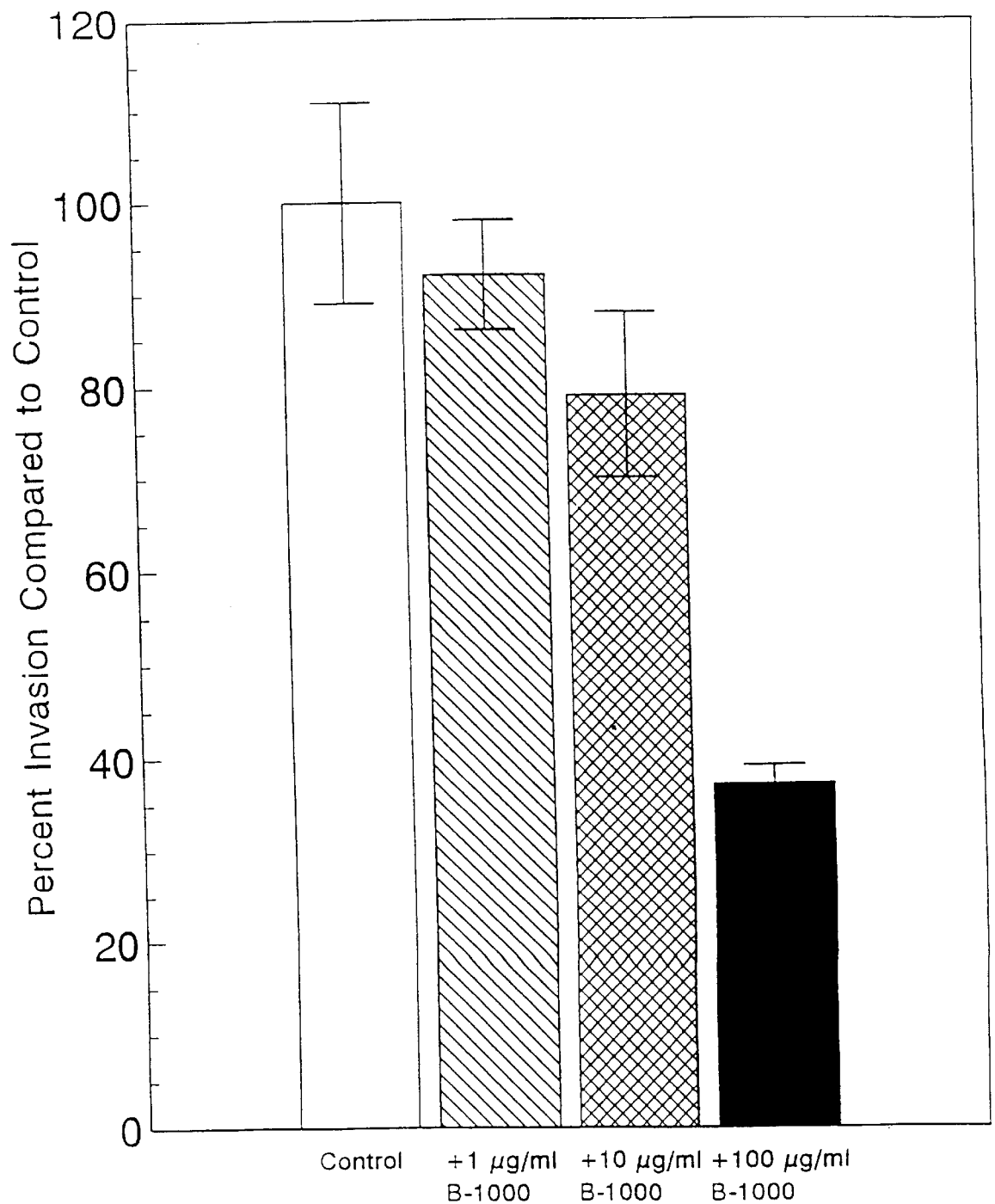
FIG. 1 shows the effect of B1000 on the invasive potential of C8161 human melanoma cells.

The sea cucumbers constitute the taxonomic Class Holothuroidea in the Phylum Echinodermata. They possess an elongated body comprising a thick, leathery body wall of epithelial and collagenous layers surrounding the internal organs or viscera, an anterior mouth surrounded by numerous retractile tentacles (herein referred to as the "flower"), and a posterior portion comprising cloaca and anus. Muscle bands are found along the length of the interior surface of the body wall.

Sea cucumbers are a well-known Chinese delicacy harvested from many areas of the world and are a valuable trading resource in Chinese-speaking countries. There are a number of patent applications by Chinese groups relating to sea cucumbers as nutritional supplements (e.g., Chinese application CN 1065019) and patents or applications from Japanese groups relating to various carbohydrate moieties from sea cucumber as anticoagulants (JP 94070085 B2; WO 9008784) and as active components for treating AIDS (WO 9202231; WO 9009181). Historically, sea cucumbers for the worldwide market have been harvested, boiled with the muscles intact, and then salted and dried over an open flame. Salting and drying are the traditional methods of obtaining a product that is safe for storage and transportation. Nutritional supplements have been prepared by finely dividing these salted and fire-dried sea cucumber body walls for use in encapsulated products.

Pharmaceutical companies are expanding efforts to screen and assay biologically active compounds from natural sources. The term that has been applied to this discovery process is "bio-prospecting." When bio-prospecting is successful in finding and identifying promising compounds, efforts are then made to determine and perfect the process by which the compound is produced in its active form. Useful processes develop from these bio-prospecting discoveries, as well as useful compositions of matter and methods of using the same.

Sea cucumber tissue has been found to be rich in numerous compounds having potential as biologically active agents in medical and veterinary applications.

These include sulfated polysaccharides (e.g. fucosylated chondroitin sulfate, Viera & Mourao, *JBC*, vol. 263, pp. 18176–83 (1988)), sterol glycosides, saponins (e.g., frondogenin and its glycosides, Findlay et al., *J. Natural Products*, vol. 47, pp. 320–324 (1984)), lactones (e.g., triterpenoids lactones, their acetates and glycosides, Findlay et al., supra), peptides, protamines, glycogens, saccharides (e.g. fucose, galactosamine, glucuronic acid, quinovose, xylose or 0-methylglucose, Findlay et al., supra), polysaccharides (e.g., polyfucose sulfate, WO 9202231) and various amorphous compounds rich in saccharide moieties (Findlay et al., supra). It has now been found that fractions derived from the sea cucumber are active inhibitors of angiogenesis. This antiangiogenic property can be used in numerous applications in research and medicine, particularly those relating to the treatment of invasive tumors and rheumatoid arthritis.

As used herein, the term "sea cucumber" refers to many species of the Phylum Echinodermata, Class Holothuroidea, such as species of the genera Actinopyga (e.g., *A. lacanora, L. echinites*), Cucumaria (e.g., *C. frondosa, C. echinata, C. chronhjelmi*), Eupentacta (e.g., *E. quinquesemita*), Halodeima (e.g., *H. cinerascens*), Holothuria (e.g., *H. pervicax, H. atra, H. edulis, H. scabra, H. monoacaria, H. leucospilota*), Leptosynapta (e.g., *L. inhaerens*), Ludwigothuria (e.g. *L. grisea*), Microthele (e.g., *M. nobilis*), Molpadia (e.g., *M. musculus*), Parastichopus (e.g., *P. nigripunctatus*), Paracaudina (e.g., *P. chilensis*), Pelagothuria, Pentacta (e.g., *P. australis*), Polycheira (e.g., *P. rufescens*), Psolus (e.g., *P. chitonoides*), Stichopus (e.g., *S. japonicus, S. chloronoyus, S. variegatus*), Synapta (e.g., *S. maculata*), Thelenota (e.g., *T. ananas*) or Thyone (e.g., *T. briareus*);

the term "flower" refers to the anterior portion of the sea cucumber comprising the mouth and retractile tentacles;

the term "B1000" refers to the isolated epithelial layer of the sea cucumber, substantially free of the flower portion, muscle, collagenous tissues and viscera;

the term "T2000" refers to the isolated flower portion of the sea cucumber, substantially free of other portions of the sea cucumber body;

the term "active derivative" refers to any compound, fraction or combination thereof, derived from a sea cucumber fraction described herein, that has antiangiogenic activity.

The sea cucumber fractions of the present invention may be in the form of powders, capsules, tablets solutions, suspensions, ointments, or any other means of delivery which those skilled in the medical and veterinary arts would deem appropriate. The formulation is dictated by the application, e.g., an application wherein a skin malignancy is treated might call for a topical formulation, whereas treatment of a liver malignancy might call for a formulation suitable for direct injection into the site of malignancy. It is well within the skill of the medical or veterinary arts to determine a suitable formulation for any particular application. Furthermore, methods of making such formulations are well-known in the art (see, e.g. *Remington's Pharmaceutical Sciences*, 18th ed., Mack Publishing Co., Easton, Pa. (1990)).

Active antiangiogenic compositions can be obtained from sea cucumber in a variety of ways. For example, sea cucumbers can first be cleaned of muscle bands and viscera, boiled (but not salted), preferably for about ½ hour, and then dried, preferably in low-heat mechanical driers such as those employing "heat pump" technology. The dried tissue can further be ground or divided as needed for ultimate use. This process decreases the sodium content of the tissue and helps protect active ingredients from degradation. This fraction can be formulated and used directly as an antiangiogenic composition, either alone or in combination with other sea cucumber fractions, or used as a raw material for further purification of active derivatives. A commercial sea cucumber body wall preparation is available from Coastside Bio Resources under the tradename "Ginseng of the Sea™."

Another active fraction can be obtained from the flower portion of the sea cucumber. During the evisceration process described above, the anterior portion ("flower") of the sea cucumber is cut away from the viscera and body wall. The isolated flower is then heated, preferably for about ½ hour, dried at low temperatures (e.g., between about 140° F. and about 180° F. using conventional drying apparatus and per se known techniques). This dried fraction, designated "T2000" by the inventor, can then be ground or divided as needed for formulation and used directly as an antiangiogenic composition, either alone or in combination with other sea cucumber fractions, or as a raw material for purification of active derivatives. The method and extent of division of the material is not critical to the invention, and can be readily determined by those skilled in the art according to the manner in which the composition will be used.

Still another antiangiogenic fraction can be obtained from the epithelial layer of the sea cucumber body wall. Muscle, viscera and flower are removed as described above, followed by isolation of the epithelial layer of the sea cucumber body wall from the harder collagenous layers beneath, preferably by one or more of the following means:

heating the body-wall in water at temperatures from about 140° F. to about 180° F., preferably at about 170° F., followed by mechanical separation by hand or machine (e.g., using machines known in the art as mincers or de-boners, which detect tissue density and separate harder tissues from softer tissues);

enzymatic hydrolytic separation, using, e.g., the organism's own digestive tract enzymes, proteases from mammalian sources, proteases from non-mammalian sources or acidic hydrolyses, preferably Alcalase (NOVO Nordisk Bio Chem, North Carolina), the enzyme preferably being in a solution of about 1% to about 10% enzyme, most preferably in a solution of about 10% enzyme;

scouring/scrubbing or de-boning processes known to those skilled in the potato or chicken processing arts.

Heating in water, followed by mechanical separation using a de-boner is most preferred.

The epithelial fraction so obtained (designated "B1000" by the inventor) is a dark, moist, viscous, carbohydrate-rich matter. B1000 can be dried as described above, formulated and used directly as an antiangiogenic composition, either alone or in combination with other sea cucumber fractions, or used as a raw material for the purification of active derivatives.

To determine and test the effective potency of fractions derived from sea cucumber body wall, epithelial layer, and flower, these fractions were dried, powdered and screened through a 100-mesh screen.

The chicken chorioallantoic membrane (CAM) assay is known to those skilled in the art as a method or procedure for demonstrating the effectiveness of an antiangiogenic substance or a substance for inhibiting angiogenesis or vascularization in an animal. In the CAM assay, a fertile chicken egg is prepared for testing by either of two procedures referred to in the art as the window (Knighton, et al. *J. Cancer*, vol. 35, pp. 347–355 (1977)) or egg culture techniques. In both techniques, the fertilized chicken eggs are maintained, typically in a humidified incubator, at a certain temperature and in a horizontal position with twice daily rotations. In the case of the window technique, an air pocket is created in the egg, often by withdrawing albumin, and by a particular day after fertilization (e.g., the eighth day), a window (e.g., 1.5–2.5 $cm^2$) is cut from the shell directly over the air pocket. The underlying shell membrane is carefully removed exposing a chorioallantoic membrane that is undamaged and free from any shell or shell membrane fragments. In the egg culture technique, sterile techniques are typically employed in transferring the fertilized egg at a particular day after fertilization to a petri dish containing a tissue culture medium. These techniques are well known to those skilled in the art.

The angiogenesis inhibitor of the present invention may be administered orally, topically, rectally or via injection, alone or in mixture with an excipient or a carrier as set forth above and in accordance with the particular purpose of use. The active ingredient should be within a range of from about 0.01 to about 100 w/w %, or more preferably, of from about 0.05 to about 80 w/w %. The dose per day thereof, also depending upon the particular use to which the composition is put, the frequency of administrations, the form of medicament, the symptoms, age and body weight of the recipient of the composition, should be within a range of from about 0.1 to about 1,500 mg of the effective ingredient per kg of body weight, preferably from about 1 to about 1,000 mg/kg and most preferably about 10 mg/kg. The daily dosage of administration may be divided into two to four separate doses.

The following examples are intended to illustrate, but in no way to limit, the invention set forth in the claims.

EXAMPLE 1

Preparation of Whole Body Wall From Sea Cucumber

Muscle meat, viscera, anterior and posterior portions of the sea cucumber *Cucumaria frondosa* were removed in order to leave a sea cucumber body wall free of most, if not all of the above named portions. The thus obtained body wall was boiled for about ½ hour in fresh water and dried in a low heat utilizing a 40 hp "heat-pump" dryer (Southwind Mfg., Nova Scotia, Canada). The body wall fraction was dried to about 3% moisture and finely divided.

EXAMPLE 2

Mechanical Extraction and Processing of Sea Cucumber Epithelium

A fraction termed B1000, consisting of sea cucumber epithelium, was produced by the following method. The anterior, posterior, viscera and muscles were removed from sea cucumbers of the species *Cucumaria frondosa* to obtain an isolated body wall. Body wall portions thus obtained were heated for about 30 minutes in fresh 170° F. water, then cooled on wire racks to room temperature. Next, the body wall portions were passed through an industrial machine known to those in the food processing arts as a de-boner or mincer (Paoli Machine, Ill.). The de-boner was adjusted to separate the softer outer epithelial layer from the harder collagenous portion of the body wall. The black viscous layer of the epithelium so separated, designated B1000 by the inventor, was dried by conventional means using a 40 hp "heat pumps" dryer as in Example 1 to approximately 3% moisture content and finely divided to obtain a powder.

EXAMPLE 3

Enzymatic Extraction and Processing of Sea Cucumber Epithelium

Enzymes were used to help separate the epithelial layer from the harder collagenous inner layer of body walls from sea cucumbers of the species *Cucumaria frondosa*. The body wall portions were isolated and heated in water as described in Examples 1 and 2. They were then soaked in a solution of 10% Alcalase (NOVO Nordisk Bio Chem, North Carolina) in fresh water at a temperature of 130° F. (±30° F.). The time of soaking depended on the condition of the particular lot of body walls and their characteristics, and varied from about 15 min. to about 3 hours. The average time soaking in the enzyme solution was about one half hour. The body walls were then removed from the enzyme solution and processed by hand to further isolate the black epithelial layer B1000 from the underlying collagenous tissues. The B1000 thus obtained was dried and powdered as in Examples 1 & 2.

EXAMPLE 4

Extraction and Processing of Sea Cucumber Flower

A fraction termed T2000, derived from the sea cucumber flower, was obtained in the following manner.

During the processing operation of removing viscera and muscle set forth in Examples 1 and 2, the anterior portion of the sea cucumber*Cucumaria frondosa* was removed, taking care to include the mouth portion of the head with surrounding tentacles, which is a tissue rich in calcium carbonate (among other compounds). This separated flower portion was then boiled for about ½ hour to obtain the fraction designated T2000 by the inventor. The T2000 was then dried in a conventional heat-pump dryer as in Examples 1–3 and finely divided.

EXAMPLE 5

Preparation of Derivative Fractions of B1000 and T2000

The finely divided powders of epithelial layer (B1000) and flower fraction (T2000) obtained in Examples 2 and 4, respectively, were further processed by mixing in an aqueous solution and rotating for 12 hours with a magnetic stirrer. The resultant solution was centrifuged at 30,000 RPM for one hour and the supernatant was removed and lyophilized.

EXAMPLE 6

Anti-Angiogenesis Using the 10-day Old Chick Embryo Chorioallantoic Membrane Assay (CAM) On Various Sea Cucumber Extracts.

Method: The conventional method used was as described in D. Knighton, D. Ausprunk, D. Tapper, and J. Folkman, "Avascular and Vascular Phases of Tumor Growth in the Chick Embryo." J. Cancer 35:347–355, 1977.

Procedure: The test compounds were suspended in sterile saline and then applied to methylcellulose discs, ¼" in diameter with a micropipette and allowed to air dry at a concentration of 1 µg/disc. A combination of hydrocortisone and heparin was used as a positive control, as this combination is well known to inhibit angiogenesis.

The test was graded as follows:

0 No change from control embryos
+1 Slight inhibition of vasculature
+2 Moderate inhibition of vasculature
+3 Almost complete inhibition of vasculature
+4 Complete inhibition of vasculature Results: The CAM Assay antiangiogenesis scores are summarized in Table I, below. The following scores are averages based on a minimum of 10 eggs used for each sample. All test samples showed antiangiogenic activity. In particular, T2000 was shown to be just as active as the control composition, while B1000 showed an activity greater than the control.

TABLE I

Antiangiogenic effect of sea cucumber fractions as determined by CAM assay

| Test Sample | Saline Blank (Neg. Ctrl.) | Hydrocortisone/Heparin (Positive Control) | Test Sample Results |
| --- | --- | --- | --- |
| sea cucumber body wall | — | 2.8 | 3.5 |
| sea cucumber body wall | 0 | 2.9 | 2.6 |
| sea cucumber body wall | 0 | 3.1 | 2.7 |
| sea cucumber body wall | 0 | 3.4 | 1.8 |
| B1000 | 0 | 3.6 | 3.8 |
| T2000 | 0 | 3.3 | 3.3 |

EXAMPLE 7

Endothelial Tubule Formation (Inhibition of Angiogenesis)

Inhibition of tubule formation was assessed by the methods of Montesano, et al., J. Cell Biol., vol. 97, pp. 1648–1652 (November 1983) (incorporated herein by reference). Endothelial cells (2000) were plated on a tissue culture slide coated with a thin layer of Matrigel according to conventional methods in the presence or absence of test compound. These slides were examined at 18 hours for the presence of tubule formation and graded by two independent observers for the presence of capillary tubules from 0 (no tubules) to 4+ (control tubules). The results are summarized in Table II. All compositions tested showed at least 90% inhibition of tubule formation. B1000 and sea cucumber body wall fraction significantly inhibited tubule formation at concentrations of 0.01% and higher as compared to control (p<0.05).

TABLE II

Endothelial tubule formation assay

| Sample | Tubule Formation |
| --- | --- |
| B1000 | 0.005 |
| T2000 | 0.005 |
| sea cucumber body wall | 0.005 |
| sea cucumber body wall | 0.005–0.2 |

EXAMPLE 8

Efficacy of B1000 as an Anti-Invasive Agent Using Human Melanoma Tumor Cell Model Invasion profiles were determined for the human melanoma tumor cell line C8161 using the Membrane Invasion Culture System (MICS) assay containing a simple matrix barrier, composed of human basement membrane components (laminin and collagen IV) in a gelatin base (Hendrix et al., Invasion Metastasis, vol. 9(5), pp. 278–97 (1989)). Cells were assayed in the presence of 1, 10 and 100 µg B1000/ml for 24 hours, and their ability to invade the basement membrane compared with a control group of untreated cells. The invasive potential of the control group was normalized to 100% and the changes in the treated groups ability to invade calculated as a percent of this value. As seen in FIG. 1, 1 and 10 µg B1000/ml resulted in a slight, though not significant decrease in the invasive potential of C8161; while at 100 µg/ml, B1000 decreased the ability of these cells to invade by the significant value of 63% inhibition.

EXAMPLE 9

Efficacy of B1000 as an Anti-Invasive Agent Using Human Rheumatoid Arthritis Cell Model Rheumatoid arthritis is a disease of the joints which some have likened to a "non-metastasizing" cancerous condition. Like cancer, rheumatoid arthritis is characterized by non-malignant cells becoming hyperproliferative which produces a tissue mass that leads to destruction of tissues. Unlike cancer, rheumatoid arthritis does not have a metastatic component. The destructive and invasive nature of rheumatoid arthritis derived cells was examined. The same three stages associated with this disease which so closely resemble what occurs in cancer were investigated.

Figure 2:
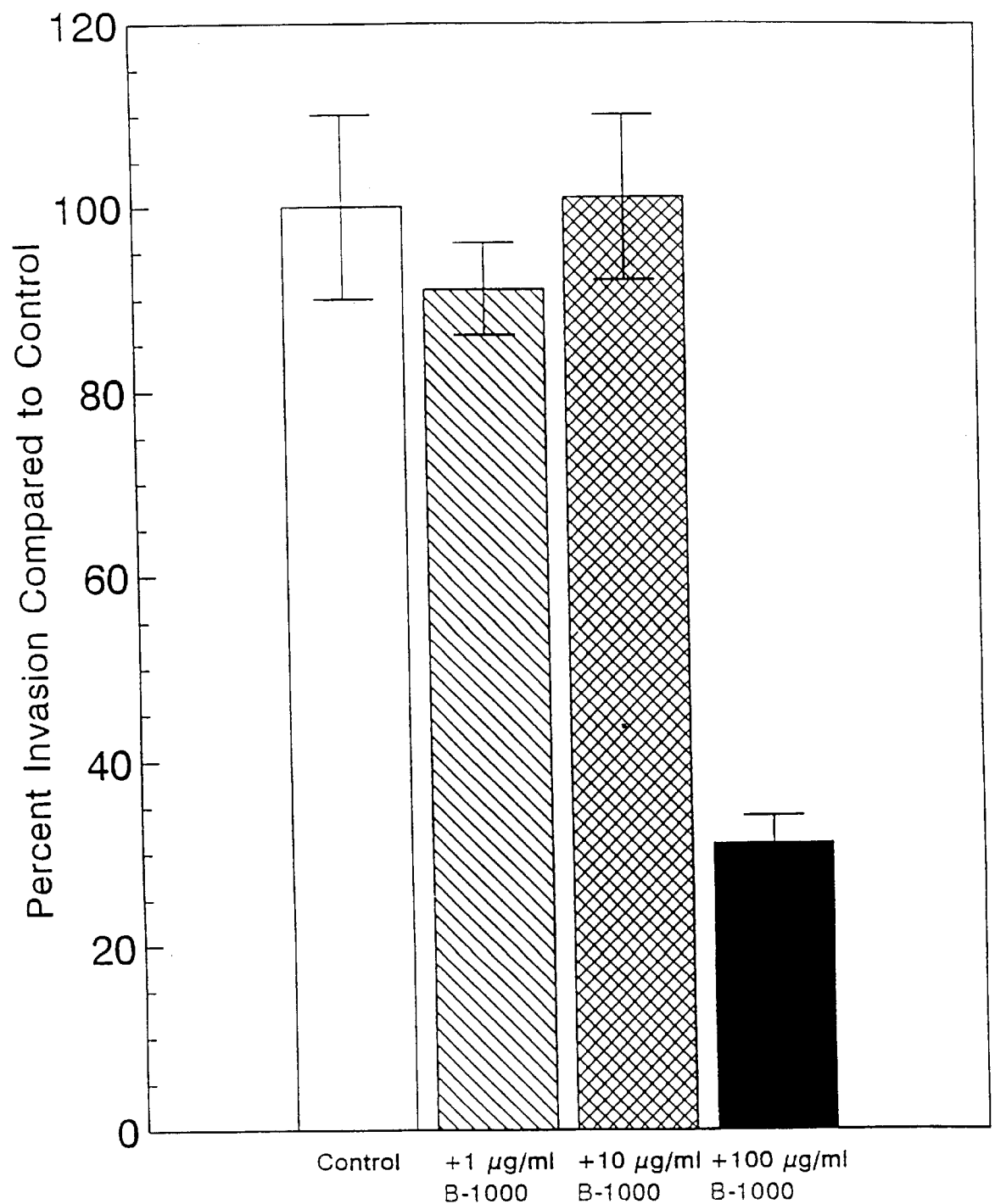
FIG. 2 shows the effect of B1000 on the invasive potential of RA116 human rheumatoid arthritis cells.

Invasion profiles were determined for the human rheumatoid arthritis synovial fibroblast cell line RA116 using the Membrane Invasion Culture System (MICS) assay containing a cartilage matrix barrier (Hendrix et al., Invasion Metastasis, vol. 9(5), pp. 278–97 (1989)). Cells were assayed in the presence of 1, 10 and 100 µg B1000/ml for 48 hours, and their ability to invade compared with a control group of untreated cells. The invasive potential of the control group was normalized to 100, and the changes in the treated groups ability to invade calculated as a percent of this value. As seen in FIG. 2, 1 and 10 µg B1000/ml caused little-to-no change in the ability of these cells to invade, while at 100 µg/ml B1000 decreased the ability of these cells to invade by the significant value of 69% inhibition.

EXAMPLE 10

Preparation from Sea Cucumber Body Wall of the Active Derivative Fucosylated Chondroitin Sulfate Fucosylated chondroitin sulfate, an active derivative of the sea cucumber body wall, was extracted from the body wall of the sea cucumber *Ludwigothurea grisea* by papain digestion, and purified by chromatography on DEAE-cellulose and Sepharose CL-4B, all according to the methods of Viera & Mourao(1988) (supra).

The body wall of *L.grisea* was carefully separated from other tissues, immersed immediately in acetone and kept for 24 hours at 4° C. The dry tissue (50g) was cut into small pieces, suspended in 1000 ml of 0.1 M sodium acetate buffer (pH 6.0) containing 5 g of papain, 5 mM EDTA, and 5 mM cysteine, and incubated at 60° C. during 24 hours. The incubation mixture was then centrifuged (2000×g for 10 minutes at 10° C.), and the clear supernatant was precipitated with 2 volumes of 95% ethanol. After maintenance at −10° C. for 24 hours, the precipitate formed was collected by centrifugation (2000×g for 15 minutes at 10° C.), vacuum dried, dissolved in 50 ml of distilled water, exhaustively dialyzed against distilled water and lyophilized. About 5 g (dry weight) of crude extract was obtained after these procedures.

About 400 mg of the crude extract was applied to a DEAE-cellulose column (7×2 cm) equilibrated with 0.1 M sodium acetate buffer (pH 5.0) and washed with 100 ml of the same buffer. The column was developed by a linear gradient prepared by mixing 80 ml of 0.1 M sodium acetate buffer (pH 5.0) with 80 ml of 0.6 M NaCl and 80 ml of 1.2 M NaCl in the same buffer. The flow rate of the column was 12 ml per hour, and fractions of 3.0 ml were collected. They were checked by the Dubois et al. (*Analytical Chemistry*, vol. 28, pp. 350–354 (1956), incorporated herein by reference) and carbazole (Dische, *JBC* vol. 167, pp. 189–198, (1947), incorporated herein by reference) reactions, and conductivity was measured. Two main fractions of sulfated glycans (F1 and F2) were obtained, dialyzed against distilled water, and lyophilized.

About 40 mg of each fraction of sulfated glycans purified by DEAE-cellulose chromatography dissolved in 1.5 ml of 0.3 M pyridine/acetate buffer (pH 5.0) was chromatographed on a Sepharose CL-4B column (115 cm×1.5 cm). Columns were eluted with the same buffer at a flow rate of 6 ml per hour and aliquots of approximately 1.5 ml were collected. The fractions were assayed by the Dubois et al. (supra) and carbazole (Dische, supra) reactions and by the metachromatic property (Albano and Mourao, *JBC* vol. 261, pp. 758–765 (1986), incorporated herein by reference). Columns were calibrated using blue dextran as a marker for $V_o$ and cresol red as a marker for $V_t$.

The fraction F-2 was found to comprise fucosylated chondroitin sulfate.

EXAMPLE 11

Antiangiogenic Activity of Fucosylated Chondroitin Sulfate Derived From Sea Cucumber Body Wall The antiangiogenic activity of the fucosylated chondroitin sulfate of Example 10 was determined using the Chorioallantoic Membrane Assay (CAM) method as set forth in Example 6. The activity of sea cucumber-derived fucosylated chondroitin sulfate was compared with that of shark cartilage chondroitin-6-sulfate (Sigma, Lot #103), a defucosylated sample prepared from the fucosylated chondroitin sulfate of Example 10, and the B1000 of Example 2. Defucosylation was carried out by mild acid hydrolysis. Fifty milligrams of the fucolysated chondroitin sulfate of Example 10 were dissolved in 1.0 ml of 150 mM $H_2SO_4$, maintained at 100° C. for 30 minutes, and the pH of the solution was adjusted to 7.0 with 0.3 ml of ice-cold 1.0 M NaOH.

The test compounds were suspended in sterile saline and then applied to methylcellulose discs ¼ in. in diameter with a micropipette and allowed to air dry at a concentration of 1 μg/disc. The test was graded as follows:

0 No change from control embryos
+1 Slight inhibition of vasculature
+2 Moderate inhibition of vasculature
+3 Almost complete inhibition of vasculature
+4 Complete inhibition of vasculature The results of the assay are set forth below in Table III. The scores are averages based on a minimum of 25 eggs used. Table III—Antiangiogenic effect of sea cucumber fucosylated chondroitin sulfate as determined by CAM assay

| Test Sample | Saline Blank (Neg. Ctrl.) | Hydrocortisone/ Heparin (Pos. Ctrl.) | Test Sample Results |
|---|---|---|---|
| Fucosylated Chondroitin Sulfate | 0.04 | 3.32 | 3.12 |
| Chondroitin 6 sulfate | 0 | 3.36 | 1.96 |
| Defucosylated sample | 0 | 3.35 | 0.12 |
| B1000 | 0 | 3.35 | 3.41 |

As can be seen from the data in the final column of Table III, sea cucumber fucosylated chondroitin sulfate shows good antiangiogenic activity. The activity seen was nearly as high as that of the positive control, hydrocortisone/heparin, and higher than that seen with shark cartilage chondroitin-6-sulfate. It is interesting to note that the activity of the fucosylated chondroitin sulfate was not as high as the activity of the B1000 body wall preparation, possibly indicating the presence of additional active antiangiogenic compounds in the sea cucumber body wall.

I claim:

1. A method of inhibiting angiogenesis in a warm blooded animal comprising administering an angiogenesis-inhibiting amount of a composition comprising an active ingredient selected from the group consisting of isolated sea cucumber body wall, isolated sea cucumber epithelial layer, isolated sea cucumber flower, combinations thereof and active derivatives thereof.

2. The method of claim 1 wherein the composition is administered in an amount per day sufficient to provide between about 10 milligrams per kilogram body weight per day and about 1 gram per kilogram body weight per day of the active ingredient.

3. The method of claim 2 wherein the composition is administered in an amount per day sufficient to provide about 10 milligrams per kilogram body weight per day of the active ingredient.

4. The method of claim 1 wherein the composition is in a dosage form suitable for administration orally, rectally, topically or via injection.

5. The method of claim 4 wherein the dosage form is suitable for oral administration.

6. The method of claim 4 wherein the dosage form is suitable for topical administration.

7. The method of claim 1 wherein the active derivative is selected from the group consisting of sulfated polysaccharides, sterol glycosides, saponins, lactones, peptides, protamines, glycogens, saccharides, polysaccharides and combinations thereof.

8. The method of claim 7 wherein the active derivative is a saponin.

9. The method of claim 7 wherein the active derivative is a sulfated polysaccharide.

10. The method of claim 9 wherein the sulfated polysaccharide is fucosylated chondroitin sulfate.

11. A method of inhibiting angiogenesis in a warm blooded animal comprising administering an angiogenesis-inhibiting amount of a composition comprising isolated sea cucumber body wall or active derivatives thereof.

12. The method of claim 11 wherein the composition is administered in an amount per day sufficient to provide between about 10 milligrams per kilogram body weight per day and about 1 gram per kilogram body weight per day of the isolated sea cucumber body wall or active derivatives thereof.

13. The method of claim 1 wherein the composition is administered in an amount per day sufficient to provide about 10 milligrams per kilogram body weight per day of the isolated sea cucumber body wall or active derivatives thereof.

14. The method of claim 11 wherein the composition is in a dosage form suitable for administration orally, rectally, topically or via injection.

15. The method of claim 14 wherein the dosage form is suitable for oral administration.

16. The method of claim 14 wherein the dosage form is suitable for topical administration.

17. The method of claim 11 wherein the active derivative is selected from the group consisting of sulfated polysaccharides, sterol glycosides, saponins, lactones, peptides, protamines, glycogens, saccharides, polysaccharides and combinations thereof.

18. The method of claim 11 wherein the active derivative is a saponin.

19. The method of claim 17 wherein the active derivative is a sulfated polysaccharide.

20. The method of claim 19 wherein the sulfated polysaccharide is fucosylated chondroitin sulfate.

21. A method of inhibiting angiogenesis in a warm blooded animal comprising administering an angiogenesis-inhibiting amount of a composition comprising isolated sea cucumber epithelial layer or active derivatives thereof.

22. The method of claim 21 wherein the composition is administered in an amount per day sufficient to provide between about 10 milligrams per kilogram body weight per day and about 1 gram per kilogram body weight per day of the isolated sea cucumber epithelial layer or active derivatives thereof.

23. The method of claim 22 wherein the composition is administered in an amount per day sufficient to provide about 10 milligrams per kilogram body weight per day of the isolated sea cucumber epithelial layer or active derivatives thereof.

24. The method of claim 21 wherein the composition is in a dosage form suitable for administration orally, rectally, topically or via injection.

25. The method of claim 24 wherein the dosage form is suitable for oral administration.

26. The method of claim 24 wherein the dosage form is suitable for topical administration.

27. The method of claim 21 wherein the active derivative is selected from the group consisting of sulfated polysaccharides, sterol glycosides, saponins, lactones, peptides, protamines, glycogens, saccharides, polysaccharides and combinations thereof.

28. The method of claim 27 wherein the active derivative is a saponin.

29. The method of claim 27 wherein the active derivative is a sulfated polysaccharide.

30. The method of claim 29 wherein the sulfated polysaccharide is fucosylated chondroitin sulfate.

31. A method of inhibiting angiogenesis in a warm blooded animal comprising administering an angiogenesis-inhibiting amount of a composition comprising isolated sea cucumber flower or active derivatives thereof.

32. The method of claim 31 wherein the composition is administered in an amount per day sufficient to provide between about 10 milligrams per kilogram body weight per day and about 1 gram per kilogram body weight per day of the isolated sea cucumber flower or active derivatives thereof.

33. The method of claim 30 wherein the composition is administered in an amount per day sufficient to provide about 10 milligrams per kilogram body weight per day of the isolated sea cucumber flower or active derivatives thereof.

34. The method of claim 31 wherein the composition is in a dosage form suitable for administration orally, rectally, topically or via injection.

35. The method of claim 34 wherein the dosage form is suitable for oral administration.

36. The method of claim 34 wherein the dosage form is suitable for topical administration.

37. The method of claim 31 wherein the active derivative is selected from the group consisting of sulfated polysaccharides, sterol glycosides, saponins, lactones, peptides, protamines, glycogens, saccharides, polysaccharides and combinations thereof.

38. The method of claim 37 wherein the active derivative is a saponin.

39. The method of claim 37 wherein the active derivative is a sulfated polysaccharide.

40. The method of claim 39 wherein the sulfated polysaccharide is fucosylated chondroitin sulfate.

* * * * *